United States Patent
Parthasarathy et al.

(10) Patent No.: US 9,607,381 B2
(45) Date of Patent: Mar. 28, 2017

(54) ACCURATE AND RAPID MAPPING OF POINTS FROM ULTRASOUND IMAGES TO TRACKING SYSTEMS

(71) Applicant: KONINKLIJKE PHILIPS N.V., Eindhoven (NL)

(72) Inventors: Vijay Parthasarathy, Mt. Kisco, NY (US); Ameet Kumar Jain, New York, NY (US); Hua Xie, Ossining, NY (US); Francois Guy Gerard Marie Vignon, Croton on Hudson, NY (US); Christopher Stephen Hall, Kirkland, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 110 days.

(21) Appl. No.: 14/416,653

(22) PCT Filed: Jul. 17, 2013

(86) PCT No.: PCT/IB2013/055859
§ 371 (c)(1),
(2) Date: Jan. 23, 2015

(87) PCT Pub. No.: WO2014/016736
PCT Pub. Date: Jan. 30, 2014

(65) Prior Publication Data
US 2015/0269728 A1 Sep. 24, 2015

Related U.S. Application Data

(60) Provisional application No. 61/676,353, filed on Jul. 27, 2012.

(51) Int. Cl.
*G06K 9/00* (2006.01)
*G06T 7/00* (2017.01)
(Continued)

(52) U.S. Cl.
CPC .......... *G06T 7/0018* (2013.01); *A61B 8/4245* (2013.01); *A61B 8/4254* (2013.01);
(Continued)

(58) Field of Classification Search
CPC ................ A61B 8/00; G01S 7/00; G06K 9/00
(Continued)

(56) References Cited

U.S. PATENT DOCUMENTS

| | | | | |
|---|---|---|---|---|
| 6,775,404 B1 * | 8/2004 | Pagoulatos | ............... | G06T 3/00 128/916 |
| 7,831,082 B2 * | 11/2010 | Holsing | ............... | G06T 7/0018 382/128 |

(Continued)

FOREIGN PATENT DOCUMENTS

| | | |
|---|---|---|
| WO | 2009063360 A1 | 5/2009 |
| WO | 2011138698 A1 | 11/2011 |
| WO | 2012001548 A1 | 1/2012 |

OTHER PUBLICATIONS

Boctor, Emad M. et al, "A Rapid Calibration Method for Registration and 3D Tracking of Ultrasound Images Using Spatial Localizer", Proc. of SPIE—The International Sociey for Optical Engineering, May 2003.

*Primary Examiner* — Abolfazl Tabatabai

(57) ABSTRACT

A method for mapping coordinates between images and tracking systems includes providing a calibration tool having a fixed geometric shape. The calibration tool includes first sensors associated with an imaging mode and second sensors associated with a tracking mode. The first and second sensors are distributed and mounted at known locations on the fixed geometric shape. The first sensors are located in a field of view of an imaging system to determine a position of the calibration tool in image space. The second sensors are tracked to determine a same position of the calibration tool in tracking space. The image space and the
(Continued)

tracking space are mapped in a common coordinate system based on artifacts of the calibration tool.

20 Claims, 5 Drawing Sheets

(51) Int. Cl.
    *A61B 8/00*     (2006.01)
    *A61B 8/08*     (2006.01)
    *G01N 29/30*     (2006.01)
    *G10K 11/00*     (2006.01)
    *G01S 7/52*     (2006.01)
    *G01S 15/89*     (2006.01)

(52) U.S. Cl.
    CPC .............. *A61B 8/481* (2013.01); *A61B 8/58* (2013.01); *G01N 29/30* (2013.01); *G06T 7/0012* (2013.01); *G01S 7/5205* (2013.01); *G01S 15/8936* (2013.01); *G06T 2207/10132* (2013.01); *G06T 2207/30004* (2013.01); *G06T 2210/41* (2013.01); *G06T 2211/428* (2013.01)

(58) Field of Classification Search
    USPC ......... 382/128–134; 600/407, 410, 411, 425, 600/427; 702/103
    See application file for complete search history.

(56) References Cited

U.S. PATENT DOCUMENTS

| | | | |
|---|---|---|---|
| 8,055,044 B2* | 11/2011 | Mielekamp | A61B 6/032 382/130 |
| 8,147,503 B2* | 4/2012 | Zhao | G06K 9/3241 382/128 |
| 2006/0241432 A1 | 10/2006 | Herline et al. | |
| 2010/0312117 A1 | 12/2010 | Fernandez | |
| 2011/0184684 A1 | 7/2011 | Li et al. | |

* cited by examiner

ACCURATE AND RAPID MAPPING OF POINTS FROM ULTRASOUND IMAGES TO TRACKING SYSTEMS

This application is a national stage application under 35 U.S.C. §371 of International Application No. PCT/IB2013/055859 filed on Jul. 17, 2013 and published in the English language on Jan. 30, 2014 as International Publication No. WO 2014/016736 A2, which claims priority to U.S. Application No. 61/676,353 filed on Jul. 27, 2012, the entire disclosures of which are incorporated herein by reference.

This disclosure relates to medical instruments and more particularly to systems and methods for rapid registration between different coordinate systems in medical or other applications.

Using ultrasound for surgical navigation requires tracking a transducer in a global coordinate system. An optical or electromagnetic (EM) tracking sensor is usually attached to the transducer, allowing position and orientation of the transducer to be tracked. A fixed mapping between the ultrasound (US) image space and the attached tracking device space needs to be determined for tracking of the ultrasound probe in space. However, many traditional mapping approaches require human interaction to identify the image coordinates of the control points. The manual procedure is time consuming because of the need for a large number of control points. This may lead to problems when commercializing and maintaining the ultrasound guidance system.

Human interaction or image processing is necessary to segment the image coordinates of the control points in ultrasound images. This segmentation is difficult due to the resolution of the tool tip as visualized in the ultrasound image, which is poor. Manual segmentation often leads to operator error in calibration and makes the calibration process tedious and time consuming. In addition, accurate mapping between two coordinate systems may need a large number of control points—which is especially difficult if the process is done manually. Further with manual interaction, intra-procedure quality control of calibration is not performed often due to the amount of time required to acquire corresponding point matches.

In accordance with the principles of the present invention, a system for mapping coordinates between images and tracking systems is provided which includes a calibration tool having a fixed geometric shape. The calibration tool includes first sensors associated with an imaging mode and second sensors associated with a tracking mode. The first and second sensors are distributed and mounted at known locations on the fixed geometric shape. An imaging system is configured to locate the first sensors in a field of view of the imaging system to determine a position of the calibration tool in image space. A tracking system is configured to track the second sensors to determine a same position of the calibration tool in tracking space. A sensor module is configured to map the image space and the tracking space in a common coordinate system based on artifacts of the calibration tool.

For example, the sensor module can calibrate registration between the image space and the tracking space using a single pose of the calibration tool. However, it is possible that the sensor module calibrates registration between the image space and the tracking space using multiple poses of the calibration tool to increase calibration accuracy. It is also possible that the sensor module calibrates registration between the image space and the tracking space by moving an imaging probe to multiple poses to increase calibration accuracy. The fixed geometric shape can include a cube and the first and second sensors can be distributed and mounted on faces of the cube. It is also possible that the fixed geometric shape includes a needle and the first and second sensors are distributed and mounted along the needle. The first sensors can include ultrasonic receivers and the image space can include an ultrasonic volume image space. The second sensors can include electromagnetic (EM) tracking sensors and the tracking space can include a generated EM field. It is also possible that the second sensors include fiber optic shape sensing sensors to determine the position of the calibration tool in tracking space. Further, it is possible that the first sensors include ultrasound receivers configured to receive a flowing contrast agent. The first sensors can be configured such that the flowing contrast agent is only visible in a head portion of the first sensors. Further still, it is possible that the calibration tool includes an interventional tool for in-vivo calibration.

Additionally, in accordance with the principles of the present invention, a method for mapping coordinates between images and tracking systems is provided which includes providing a calibration tool having a fixed geometric shape. The calibration tool includes first sensors associated with an imaging mode and second sensors associated with a tracking mode. The first and second sensors are distributed and mounted at known locations on the fixed geometric shape. The first sensors are located in a field of view of an imaging system to determine a position of the calibration tool in image space. The second sensors are tracked to determine a same position of the calibration tool in tracking space. The image space and the tracking space are mapped in a common coordinate system based on artifacts of the calibration tool.

For example, mapping can include calibrating registration between the image space and the tracking space using a single pose of the calibration tool. It is also possible that the mapping includes calibrating registration between the image space and the tracking space using multiple poses of the calibration tool to increase calibration accuracy. Further, mapping can include calibrating registration between the image space and the tracking space by moving an imaging probe to multiple poses to increase calibration accuracy. The fixed geometric shape can include a cube and the first and second sensors can be distributed and mounted on faces of the cube. It is also possible that the fixed geometric shape includes a needle and the first and second sensors are distributed and mounted along the needle. The first sensors can include ultrasonic receivers and the image space can include an ultrasonic volume image space. Second sensors can include electromagnetic (EM) tracking sensors and the tracking space can include a generated EM field. It is also possible that the second sensors include fiber optic shape sensing sensors and tracking the second sensors includes determining the position of the calibration tool in tracking space using feedback from the fiber optic shape sensing sensors. Further, the first sensors can include ultrasound receivers configured to receive a flowing contrast agent, and the method can further include pumping the contrast agent through the ultrasound receivers, for example.

Also in accordance with the principles of the present invention, another method for mapping coordinates between images and tracking systems is provided which includes providing a calibration tool having a fixed geometric shape, the calibration tool including ultrasonic receivers configured to appear in ultrasonic images and tracking sensors associated with a tracking mode, the ultrasonic receivers and the tracking sensors being distributed and mounted at known locations on the fixed geometric shape; locating the ultrasonic receivers in a field of view of an ultrasonic imaging system relative to a tracked ultrasonic probe to determine a position of the calibration tool in image space; tracking the tracking sensors to determine a same position of the calibration tool in tracking space; and mapping the image space and the tracking space in a common coordinate system based on artifacts of the calibration tool by transforming a coordinate system of the calibration tool to the tracked ultrasonic probe in both the image space and the tracking space.

For example, mapping can include calibrating registration between the image space and the tracking space using a single pose of the calibration tool. However, it is also possible that mapping includes calibrating registration between the image space and the tracking space using multiple poses of the calibration tool to increase calibration accuracy. Further, it is also possible that mapping includes calibrating registration between the image space and the tracking space by moving the tracked probe to multiple poses to increase calibration accuracy. The fixed geometric shape can include a cube and the ultrasonic receivers and the tracking sensors can be distributed and mounted on faces of the cube. It is also possible that the fixed geometric shape includes a needle and the ultrasonic receivers and the tracking sensors are distributed and mounted along the needle. The tracking sensors can include electromagnetic (EM) tracking sensors and the tracking space can include a generated EM field. It is also possible that the tracking sensors include fiber optic shape sensing sensors and tracking the tracking sensors includes determining the position of the calibration tool in tracking space using feedback from the fiber optic shape sensing sensors. Further, the ultrasonic receivers can be configured to receive a flowing contrast agent, and the method can further include pumping the contrast agent through the ultrasound receivers, for example.

These and other objects, features and advantages of the present disclosure will become apparent from the following detailed description of illustrative embodiments thereof, which is to be read in connection with the accompanying drawings.

This disclosure will present in detail the following description of preferred embodiments with reference to the following figures wherein.

Figure 7:
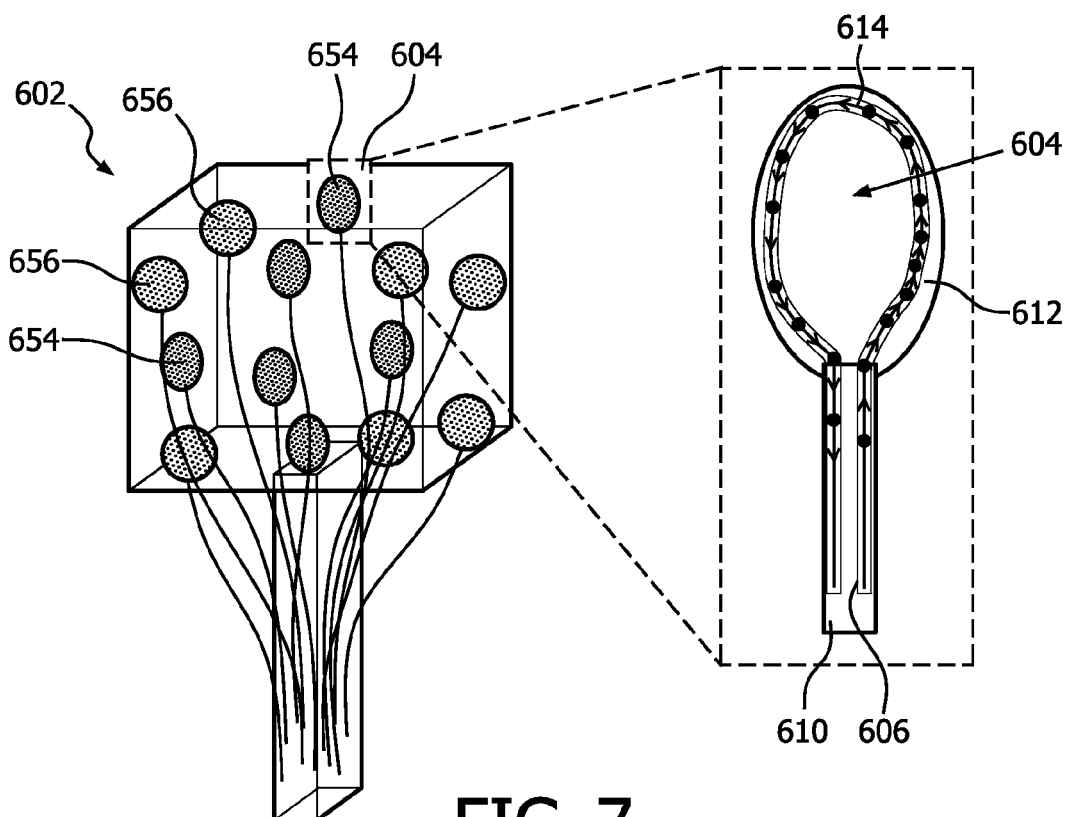
Figure 8:
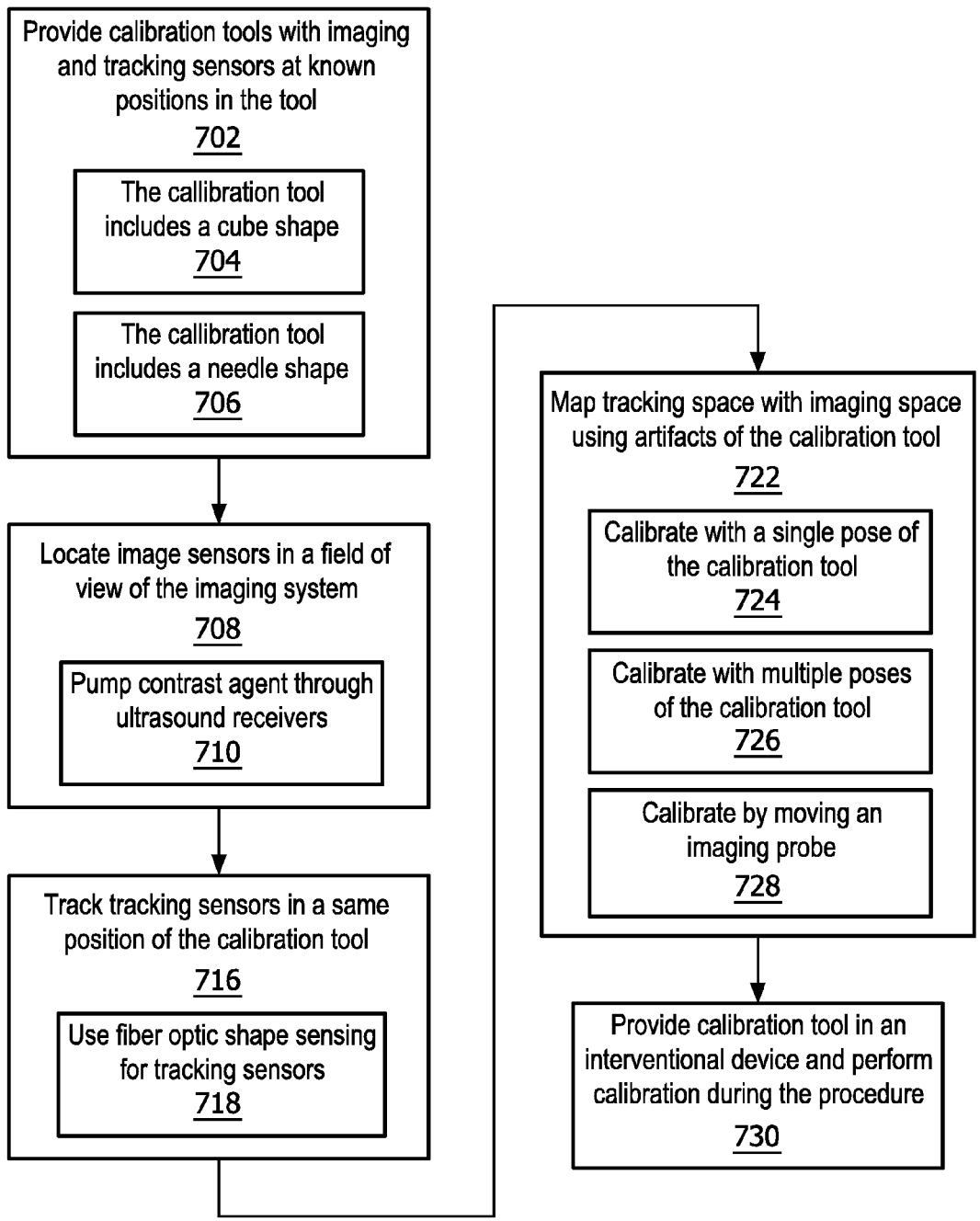

FIG. 7 is a perspective view showing an illustrative calibration device or tool using ultrasonic contrast agent as a way of imaging the calibration device in an imaging mode in accordance with one embodiment; and FIG. 8 is a flow diagram showing a method for mapping or registration between tracking and imaging coordinate systems using a calibration device or tool in accordance with preferred embodiments.

In accordance with the present principles, systems and methods are provided to collect a very high number of control points automatically to enable rapid and automatic mapping of image space to tracking space in medical and other procedures. A tool is provided that includes one or more ultrasound sensors (passive or active) embedded therein. These sensors can be localized with sub-millimeter accuracy. The tool also includes spatial tracking sensors embedded therein, which can be factory calibrated with respect to the ultrasound sensors. This enables rapid automatic co-localization of the tracking and ultrasound sensors, which could even be performed with only a single ultrasound snapshot view of the tool.

This tool can be used ex-vivo or in-vivo for automatic system setup during a procedure. The present principles may be employed to completely remove the need for segmenting the tool tip thereby increasing the ease-of-use. In addition, the present principles increase speed and accuracy of co-localization due to reduced operator error and increase robustness due to the ability of rapidly collecting many control points in a robust mapping between two coordinate systems.

It should be understood that the present invention will be described in terms of medical instruments; however, the teachings of the present invention are much broader and are applicable to any imaging and tracking combination instruments or systems. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1:
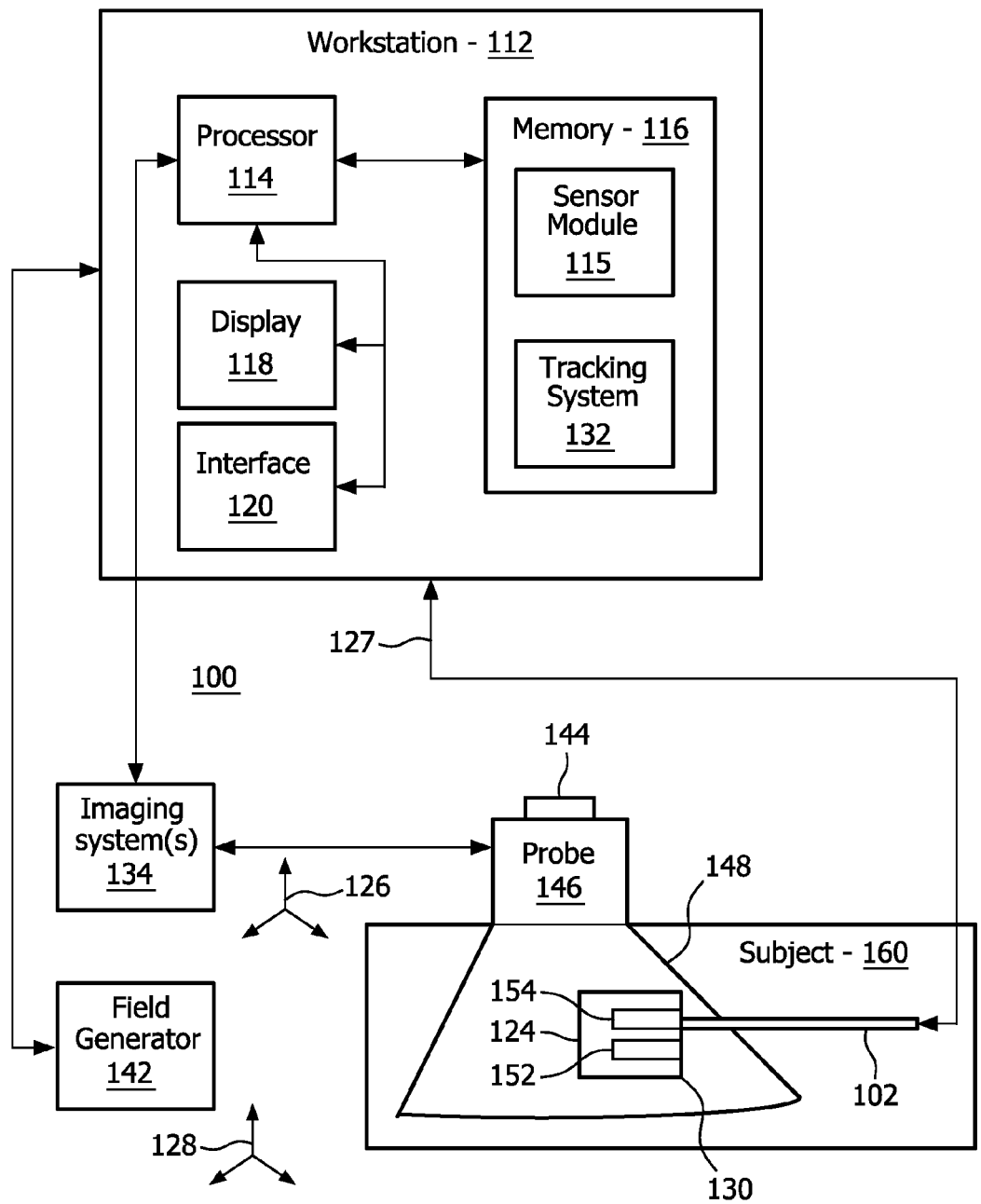
FIG. 1 is a block/flow diagram showing a coordinate system mapping or registration system which employs a calibration device or tool in accordance with the present principles.

Referring now to the drawings in which like numerals represent the same or similar elements and initially to FIG. 1, a system 100 for calibrating operative space by registration between imaging and tracking systems is illustratively shown in accordance with one embodiment. System 100 may include a workstation or console 112 from which a procedure is supervised and/or managed. Workstation 112 preferably includes one or more processors 114 and memory 116 for storing programs and applications. A sensor module 115 may be stored in memory 116 or be included as a separate unit. The sensor module 115 receives data from a smart calibration device or tool 130, an imaging system 134 and a tracking system 132 to interpret a position and orientation of the calibration device and to register coordinate systems of the imaging system 134 and the tracking system 132. The sensor module 115 is configured to receive feedback from at least two systems, and additional systems may be employed as well. The sensor module 115 can transform one coordinate system to the other, transform the local coordinate systems to a common global coordinate system or employ intermediate or other coordinate systems, as the case may be.

In one particularly useful embodiment, the two systems include the tracking system 132 and the imaging system 134. The tracking system 132 may include an electromagnetic (EM) tracking system which would include a field generator 142 and tracking sensors (e.g., coils) to track spatial positions in a tracking coordinate space. Other tracking systems may include optical tracking systems, optical shape sensing systems or any other suitable tracking system. In this embodiment, EM tracking sensors include a sensor 144 on an imaging probe 146 (other imaging modalities are also contemplated) and sensor(s) 152. The imaging system 134 may include an ultrasonic imaging system, which employs the probe 146 for imaging structures, such as internal organs or the like, to image structures in imaging coordinate space.

Figure 2:
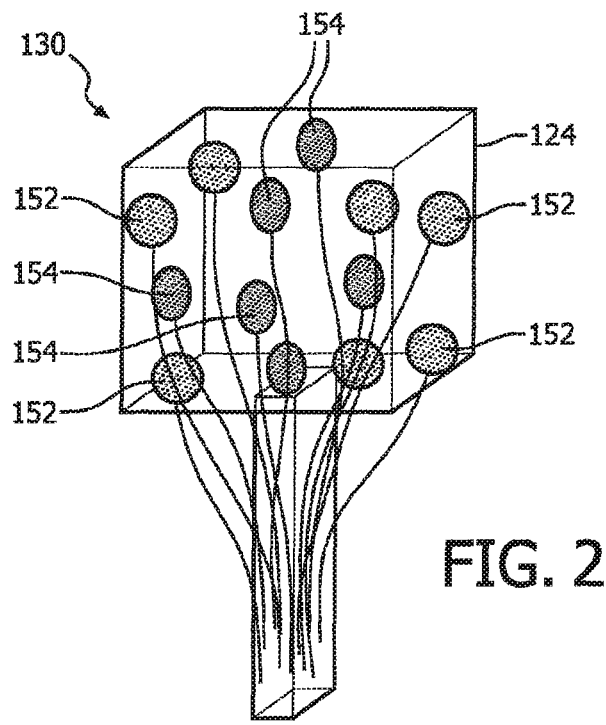
FIG. 2 is a perspective view showing an illustrative calibration device or tool in accordance with one embodiment.

Referring to FIG. 2 with continued reference to FIG. 1, the smart calibration device 130, for this example, includes EM sensors 152 and ultrasonic sensors (receivers) 154 with known geometric relationships within the device 130. The smart calibration device or tool 130 creates or leaves images or tracking signal artifacts to permit registration between the respective coordinate systems. The EM sensors 152 and receivers 154 are preferably passive devices that react to the fields or energy provided to them by their respective systems. The device 130 preferably includes a known or distinctive shape so that the geometry and its orientation can be distinguished in different coordinate systems. In one embodiment, the device 130 includes a fixed geometric housing 124, such as a cube, having sensors 152 and/or receivers 154 disposed thereon or therein. In the case of a cube, the sensors 152 and/or receivers 154 are disposed on or near each face of the cube. Other fixed geometric shapes for the tool 130 include a needle shape, oval shapes, circular shapes, etc.

The device 130 provides a rapid, accurate, and robust mapping of an ultrasonic (US) imaging coordinate system 126 (e.g., based on an origin defined at the probe 146) to a tracking space coordinate system 128 (e.g., based on an origin defined at the field generator 142). Other origins may be employed instead of or in addition to the examples given. The device 130 may include a factory calibrated arrangement of one or more of the passive ultrasound receivers 154 and EM sensors 152. These receivers 154 and/or sensors 152 may be disposed externally or internally to the device 130. The device 130 may be employed for pre-procedural calibration (externally to a patient) or as an interventional tool for in-vivo quality control of calibration.

The position of the ultrasound sensors 154 can be identified with high resolution (e.g., sub millimeter) and can be registered to the EM tracking positions, thereby increasing the accuracy of the calibration. Given the ease of use of the device 130, the ability to acquire a large number of measurements is possible in a short period of time, which makes the calibration more robust by mapping coordinate systems for rapid calibration of the US probe pre-procedurally or for rapidly checking for the fidelity of the calibration intra-procedurally. The device 130 may be employed for both 2D and 3D images.

In one embodiment of the device 130, multiple EM (e.g., five degrees of freedom (DOF)) sensors 152 and passive ultrasound receivers 154 are embedded in a tool such that the configuration of these sensors 152, 154 can be calibrated to each other during the manufacturing process. These ultrasound receivers 154 can be identified with sub-mm accuracy when brought into a field of the view of the ultrasound volume 148 (the window produced by the probe 146 or other source).

When the device 130 is brought into the field of the view of the ultrasound volume 148, even a single image of the device 130 is sufficient to get a rapid mapping of the two coordinate systems (e.g., imaging and tracking coordinate systems). This leads to the ability to provide a rapid calibration. If more accurate or robust co-localization is needed, the ultrasound probe 146 and the device 130 can be moved relative to each other while simultaneously recording measurements of one or more of: the probe's EM tracker 144, the EM sensors 152 on the device 130 and/or the position of the ultrasound receivers 154 in the US volume 148. At each configuration of the probe 146, the ultrasound sensors 154 should remain visible in the US volume 148. This continuous data collection yields a rich set of data for point registration of the two sets thereby yielding an accurate and robust ultrasound mapping between the imaging coordinate system 126 and the tracking coordinate system 128.

As described, the device 130 may include a separate designated calibration instrument or may be included in an interventional medical device or instrument 102. The medical device 102 may include a catheter, a guidewire, a probe, an endoscope, a robot, an electrode, a filter device, a balloon device, or other medical component, etc.

In one embodiment, workstation 112 records accumulated position data as to where the device 130 has been within the volume 148. Workstation 112 may include a display 118 for viewing internal images of a subject (patient) or volume 148 and may include US images as an overlay or other rendering which also shows the device 130 and its positions. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

The system 100 may be employed for rapid mapping of the imaging system 134 (e.g., ultrasound) to the tracking system 132. The device 130 can be used for one-time calibrations (say, in a factory) as well as in periodic calibration checks as a part of quality control service check for the probes or other equipment. In addition, the present embodiments may be used to do quality control checks on ultrasound calibration while the instrument is inside a body. The present principles can be applied to the field of image-guided surgery, particularly surgical intervention that employs guidance and fusion of images with other coordinate systems (e.g., other image modalities and tracking systems). The present principles may also be employed in analyzing mechanical systems including anatomical models, training models, engines, other devices, etc.

Figure 3:
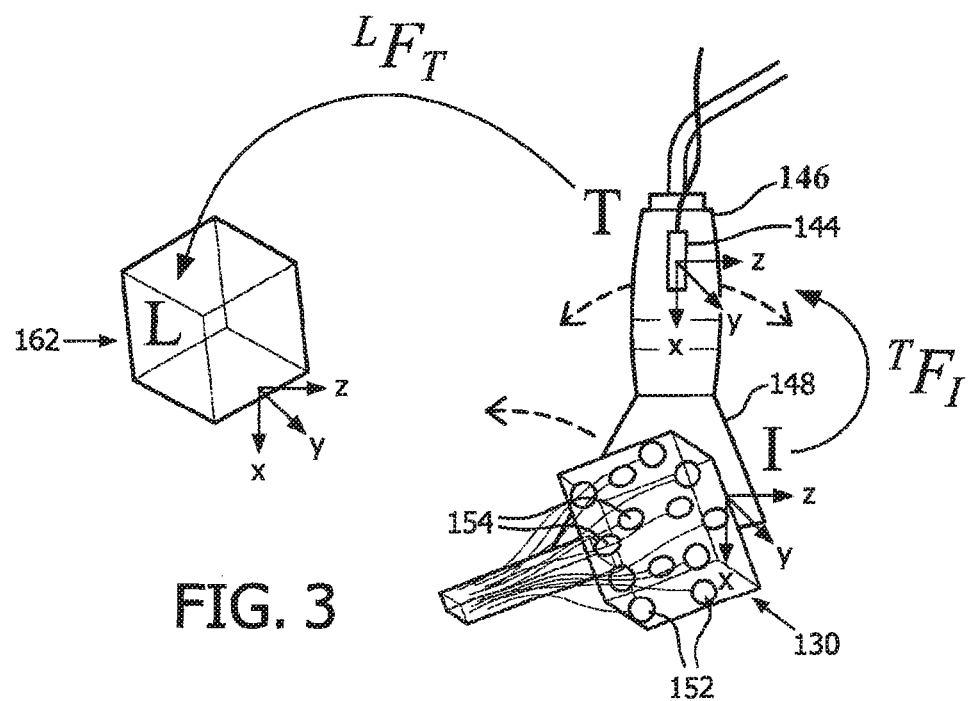
FIG. 3 is a perspective view showing an illustrative calibration device or tool in an imaging field of view during a calibration procedure in accordance with one embodiment.

Referring to FIG. 3, a schematic diagram shows an illustrative example for registering coordinate systems using the device 130. The device 130 is moved into the US field of view or volume 148. The device 130 is also within the field generated by the field generator 142 (FIG. 1). The probe 146 includes the EM tracker 144 mounted thereon. In this way, the EM sensors 152 can provide a reference position and orientation relative to the EM sensor 144 on the probe 146 and ultimately to a global coordinate reference (L) 162 for the tracking system space (T). Likewise, the device 130 and the US receivers 154 produce a visual effect in the US image. This permits a relative position between the probe 146 and the device 130 (and/or its sensors 154) in image space (I). Since the orientation of the device 130 is known and is the same in both regimes, registration between the two regimes and/or to a global coordinate system 162 is provided. FIG. 3 illustratively shows a transform TFI from the image space (I) to the tracking space (T) and a transform LFT from the tracking space (T) to the global reference (L).

Figure 4:
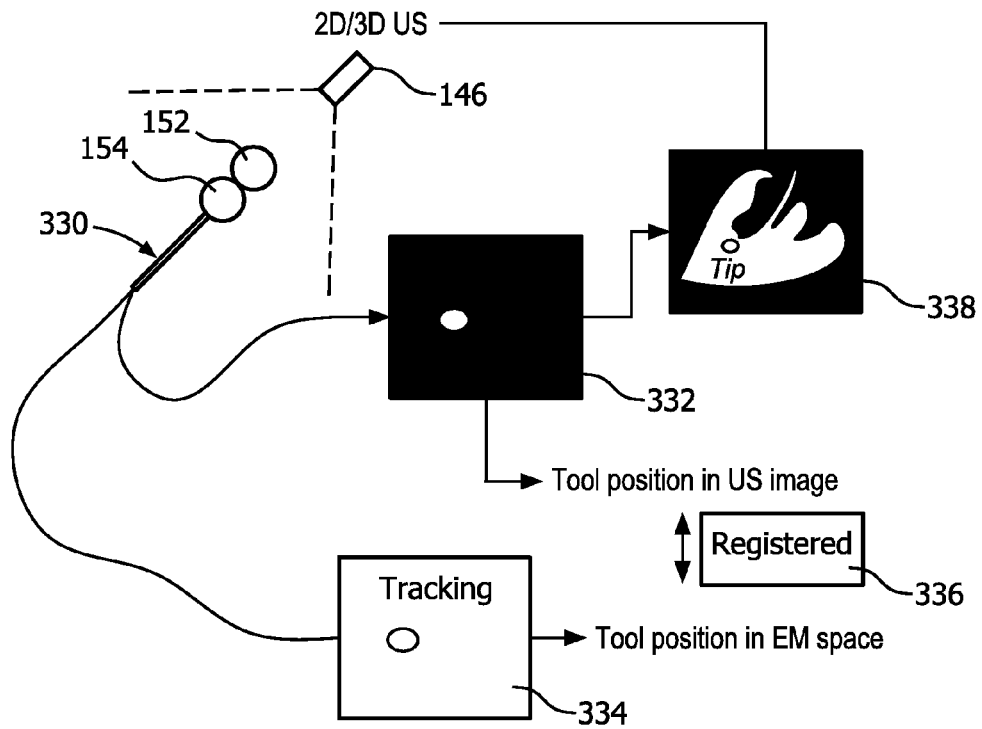
FIG. 4 is a perspective view showing another illustrative calibration device or tool in an imaging field of view during a calibration procedure in accordance with one embodiment.

Referring to FIG. 4, another embodiment of the device 130 includes a needle type device 330. In this case, one or more pairs of an EM sensor 152 and a passive ultrasound receiver 154 are embedded in or mounted on the device 330. The workflow will be similar to the workflow described above for calibrating and mapping the tracking and imaging systems. At least three images of the needle device 330 are needed to perform the mapping with the single pair configuration. This is due to the geometry of the needle device 330. The needle device 330 can be placed in different positions and orientations with respect to the ultrasound probe 146 and simultaneous readings of the EM sensor (152) position and the receiver (154) position can be recorded simultaneously. The position(s) of the needle device 330 in image space 332 and tracking space 334 can be registered in block 336 using the collected data. To assist in visualization, an overlay image 338 may be displayed showing the location of the US sensor 154.

Figure 5:
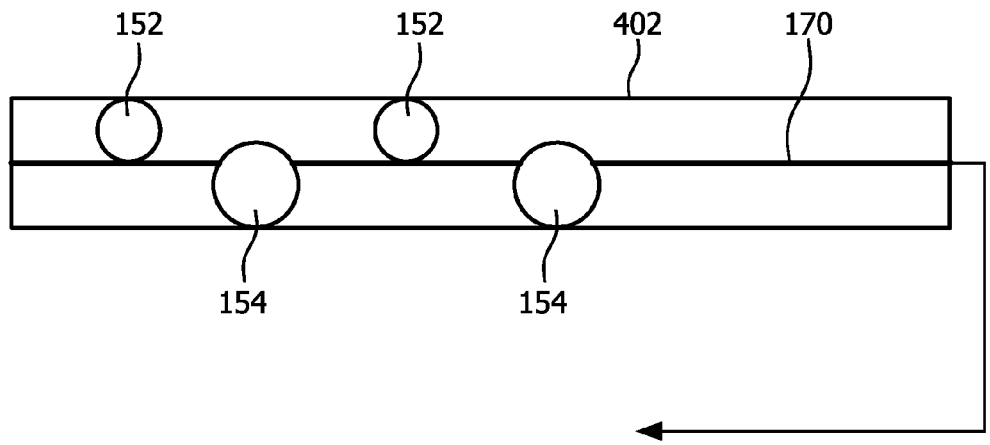
FIG. 5 is a side view showing an illustrative calibration device or tool incorporated into an interventional device in accordance with one embodiment.

Referring to FIG. 5, in another embodiment, a constellation of sensors, both EM sensors 152 and passive ultrasound receivers 154, may be embedded in an interventional tool 402. The workflow will be similar to the workflow described. This tool 402 is particularly useful for imaging/tracking inside a body. The tracking system may include an EM tracking system with sensors 152 and/or an optical shape sensing system 170. The optical shape sensing system may be employed with the sensors 152 or to replace the sensors 152. By moving the interventional tool 402 around the ultrasound field of view (FOV), a rapid calibration can be obtained and then compared with the baseline calibration that was obtained pre-procedure to make sure the calibration still maintains fidelity.

Figure 6:
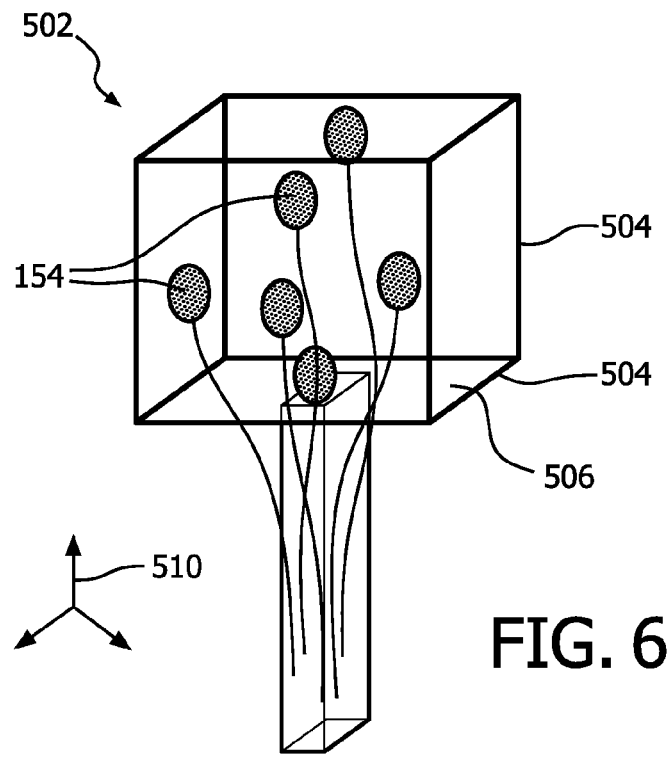
FIG. 6 is a perspective view showing an illustrative calibration device or tool using fiber optic shape sensing as a tracking mode in accordance with one embodiment.

Referring to FIG. 6, in another embodiment, a smart calibration device or tool 502, similar to device 130, includes embedded ultrasound receivers 154 and an optical shape sensing system with optical fiber or fibers 504. For illustrative purposes, the optical shape sensing fiber 504 is depicted extending along corners of a cube-shaped housing 506 of the device 502. It should be understood that the shape sensing fiber 504 may have other configurations and that the housing 506 may include other shapes. Using the same technique as described in the other embodiments, this device 502 can be used to calibrate the coordinate system of the ultrasound image to an optical shape sensing coordinate system 510 in place of the EM tracking coordinate system.

Referring again to FIG. 1 with continued reference to FIG. 6, the optical shape sensing system on device 502 includes one or more optical fibers 504 which are coupled to the device 502 in a set pattern or patterns. The optical fibers 504 connect to the workstation 112 through cabling 127. The cabling 127 may include fiber optics, electrical connections, other instrumentation, etc., as needed.

The shape sensing system with fiber optics 504 may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. A multitude of FBG sensors can be located over the length of the fiber, and multiple cores may be employed together in a same sheath (e.g., 3 or more fiber sensing cores). From the strain measurement of each FBG, the curvature of the structure can be inferred at that position. From the multitude of measured positions, the total three-dimensional form is determined so that the position and orientation of the device 502 will be known.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

Referring to FIG. 7, in another embodiment, a smart calibration device 602, similar to device 130, includes embedded ultrasound sensors 654 and EM sensors 656. The ultrasound sensors 654 are configured to include circulating contrast agent 614. Each ultrasound sensor 654 includes a head portion 604 which has a "closed loop" irrigation system 606. The irrigation system 606 permits circulation of the ultrasound contrast agent 614. The head portion 604 is connected to a stem 610 or other support member. The stem 610 and head portion 604 include tubing 612 that communicates with a pump (not shown) that circulates the contrast agent 614. The stem 610 and/or head portion 604 are designed to be hypo echoic in ultrasound so that only the ultrasound contrast agent 614 in the head portion 604 is visible in ultrasound images. The head portion 604 of the sensor 654 may be made from materials that are ultrasound transparent. The size of the head portion 604 of the sensor depends on the ultrasound frequency and should include sub millimeter dimensions, e.g., approximately 0.1-0.2 mm.

Referring to FIG. 8, methods for mapping coordinates between imaging and tracking systems are shown. In block 702, a calibration tool is provided having a fixed geometric shape. The calibration tool includes first sensors associated with an imaging mode and second sensors associated with a tracking mode. The first and second sensors are distributed and mounted at known locations on the fixed geometric shape.

In block 704, the fixed geometric shape may include a cube and the first and second sensors are distributed and mounted on faces of the cube. In block 706, the fixed geometric shape may include a needle and the first and second sensors are distributed and mounted along the needle. Other geometric shapes are also contemplated.

In block 708, the first sensors are located in a field of view of an imaging system to determine a position of the calibration tool in image space. The first sensors may include ultrasonic receivers and the image space may include an ultrasonic volume image space. In one embodiment, the first sensors include ultrasound receivers configured to receive a flowing contrast agent. In block 710, the contrast agent is pumped through the ultrasound receivers to render the receivers visible in ultrasonic images.

In block 716, the second sensors are tracked to determine a same position of the calibration tool in tracking space. The second sensors may include electromagnetic (EM) tracking sensors and the tracking space may include a generated EM field. The second sensors may include fiber optic shape sensing sensors, and in block 718, the position of the calibration tool in tracking space may be determined using feedback from the fiber optic shape sensing sensors.

In block 722, the image space and the tracking space are mapped in a common coordinate system based on artifacts of the calibration tool. In block 724, mapping includes calibrating registration between the image space and the tracking space using a single pose of the calibration tool. In block 726, mapping includes calibrating registration between the image space and the tracking space using multiple poses of the calibration tool to increase calibration accuracy. In block 728, mapping includes calibrating registration between the image space and the tracking space by moving an imaging probe to multiple poses to increase calibration accuracy. The imaging probe may include an ultrasonic probe, and the ultrasonic probe may also be tracked.

In block 730, a procedure, such as an interventional procedure, may be performed. The calibration tool may be employed for calibration ex-vivo or in-vivo. The calibration tool may include or be included on an interventional tool and be employed for in-vivo recalibration.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for accurate and rapid mapping of points from ultrasound images to tracking systems (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for mapping coordinates between images and tracking systems, comprising:

a calibration tool having a fixed geometric shape, the calibration tool including first sensors associated with an imaging mode and second sensors associated with a tracking mode, the first and second sensors being distributed and mounted at known locations on the fixed geometric shape;

an imaging system configured to locate the first sensors in a field of view of the imaging system to determine a position of the calibration tool in image space;

a tracking system configured to track the second sensors to determine a same position of the calibration tool in tracking space; and a processor configured to map the image space and the tracking space in a common coordinate system based on artifacts of the calibration tool.

2. The system as recited in claim 1, wherein the processor is configured to calibrate registration between the image space and the tracking space using a single pose of the calibration tool.

3. The system as recited in claim 1, wherein the fixed geometric shape includes a cube and the first and second sensors are distributed and mounted on faces of the cube.

4. The system as recited in claim 1, wherein the first sensors include ultrasonic receivers and the image space includes an ultrasonic volume image space.

5. The system as recited in claim 1, wherein the second sensors include electromagnetic tracking sensors and the tracking space includes a generated electromagnetic field.

6. The system as recited in claim 1, wherein the processor is configured to calibrate registration between the image space and the tracking space using multiple poses of the calibration tool to increase calibration accuracy.

7. The system as recited in claim 1, wherein the processor is configured to calibrate registration between the image space and the tracking space by moving an imaging probe to multiple poses to increase calibration accuracy.

8. The system as recited in claim 1, wherein the second sensors include fiber optic shape sensing sensors to determine the position of the calibration tool in tracking space.

9. The system as recited in claim 1, wherein the fixed geometric shape includes a needle and the first and second sensors are distributed and mounted along the needle.

10. The system as recited in claim 1, wherein the first sensors include ultrasound receivers configured to receive a flowing contrast agent.

11. The system as recited in claim 10, wherein the first sensors are configured such that the flowing contrast agent is only visible in a head portion of the first sensors.

12. The system as recited in claim 1, wherein the calibration tool includes an interventional tool for in-vivo calibration.

13. The system of claim 1, wherein at least one sensor of the first sensors includes a head connected to a support and a tubing configured to receive circulating contrast agent.

14. The system of claim 1, wherein the head and the support are configured such that only the circulating contrast agent in the head is visible in ultrasound images.

15. A method for mapping coordinates between images and tracking systems, comprising acts of:
providing a calibration tool having a fixed geometric shape, the calibration tool including first sensors associated with an imaging mode and second sensors associated with a tracking mode, the first and second sensors being distributed and mounted at known locations on the fixed geometric shape;
locating the first sensors in a field of view of an imaging system to determine a position of the calibration tool in image space;
tracking the second sensors to determine a same position of the calibration tool in tracking space; and
mapping the image space and the tracking space in a common coordinate system based on artifacts of the calibration tool.

16. The method as recited in claim 15, wherein the mapping act includes an act of calibrating registration between the image space and the tracking space using one of a single pose of the calibration tool and multiple poses of the calibration tool, and wherein the fixed geometric shape includes at least one of a cube, with the first and second sensors distributed and mounted on faces of the cube, and a needle, with the first and second sensors are distributed and mounted along the needle.

17. The method of claim 15, wherein the mapping act includes an act of calibrating registration between the image space and the tracking space by moving an imaging probe to multiple poses to increase calibration accuracy.

18. A method for mapping coordinates between images and tracking systems, comprising acts of:
providing a calibration tool having a fixed geometric shape, the calibration tool including ultrasonic receivers configured to appear in ultrasonic images and tracking sensors associated with a tracking mode, the ultrasonic receivers and the tracking sensors being distributed and mounted at known locations on the fixed geometric shape;
locating the ultrasonic receivers in a field of view of an ultrasonic imaging system relative to a tracked ultrasonic probe to determine a position of the calibration tool in image space;
tracking the tracking sensors to determine a same position of the calibration tool in tracking space; and
mapping the image space and the tracking space in a common coordinate system based on artifacts of the calibration tool by transforming a coordinate system of the calibration tool to the tracked ultrasonic probe in both the image space and the tracking space.

19. The method of claim 18, wherein the mapping act includes an act of calibrating registration between the image space and the tracking space using one of a single pose of the calibration tool and multiple poses of the calibration tool, and wherein the fixed geometric shape includes at least one of a cube, with the first and second sensors distributed and mounted on faces of the cube, and a needle, with the first and second sensors are distributed and mounted along the needle.

20. The method of claim 18, wherein the mapping act includes an act of calibrating registration between the image space and the tracking space by moving the tracked ultrasonic probe to multiple poses to increase calibration accuracy.

* * * * *